United States Patent [19]
Ruud et al.

[11] Patent Number: 5,414,747
[45] Date of Patent: May 9, 1995

[54] METHOD AND APPARATUS FOR IN-PROCESS ANALYSIS OF POLYCRYSTALLINE FILMS AND COATINGS BY X-RAY DIFFRACTION

[75] Inventors: Clayton O. Ruud, State College, Pa.; Mark E. Jacobs, Wheelersburg, Ohio

[73] Assignee: The Penn State Research Foundation, University Park, Pa.

[21] Appl. No.: 189,464

[22] Filed: Jan. 31, 1994

Related U.S. Application Data

[63] Continuation-in-part of Ser. No. 20,480, Feb. 22, 1993.

[51] Int. Cl.$^6$ .................................. G01N 23/207
[52] U.S. Cl. .............................. 378/73; 378/72; 378/83
[58] Field of Search ................ 378/71, 72, 73, 81, 378/83, 88, 89

[56] References Cited

U.S. PATENT DOCUMENTS

| | | |
|---|---|---|
| 3,855,470 | 12/1974 | Sahores et al. . |
| 4,064,437 | 12/1977 | Hirose et al. . |
| 4,301,364 | 11/1981 | Goebel . |
| 4,686,631 | 8/1987 | Ruud . |
| 4,910,758 | 3/1990 | Herrick . |
| 5,003,569 | 3/1991 | Okada et al. . |
| 5,125,016 | 6/1992 | Korhonen et al. ............ 378/72 |
| 5,148,458 | 9/1992 | Ruud . |
| 5,187,727 | 2/1993 | Vogler et al. . |
| 5,193,104 | 3/1993 | Bastie et al. .................. 378/73 |

OTHER PUBLICATIONS

Yeager et al., "The Determination of Three-Dimensional Stress Tensors on Multilayer Thin Films," *Journal of Nondestructive Evaluation*, vol. 10, No. 3, 1991, pp. 79–87.

Rudd et al., "Application of an Advanced XRD Instrument for Surface Stress-Tensor Measurements," *Experimental Mechanics*, vol. 25, No. 3, Sep. 1985, pp. 245–250.

Rudd et al., "Nondestructive Characterization of Beta Silicon Carbide CVD Coatings," *Review of Progress in Quantitative Nondestructive Evaluation*, vol. 8B, pp. 1369–1376.

Ruud et al., "A Miniature Instrument for Residual Stress Measurement," *Advances in X-Ray Analysis*, vol. 27, pp. 273–283, 1984.

B. D. Cullity, "Measurement of Residual Stress," *Elements of X-Ray Diffraction*, pp. 447–459.

C. O. Ruud, "Position-sensitive detector improves x-ray powder diffraction," *Industrial Research & Development*, Jan. 1983, pp. 84–87.

Rudd et al., "An XRPD Investigation of a Face-Centered Cubic Metallic Plating," *Powder Diffraction*, vol. 1, No. 2, Jun. 1986, pp. 22–27.

Kozaczek et al., "Characterizing the Deformation of Cold-Rolled Copper Sheet," *The Journal of the Minerals, Metals & Materials Society*, vol. 42, No. 5, May, 1990, pp. 35–38.

Ruud et al., "Simultaneous Residual Stress and Retained Austenite Measurement by X-Ray Diffraction,"

(List continued on next page.)

*Primary Examiner*—David P. Porta
*Attorney, Agent, or Firm*—Thomas J. Greer, Jr.

[57] ABSTRACT

An accurate, real-time method for monitoring and analyzing crystalline specimens having polycrystalline platings. The method is capable of individual or simultaneous analysis of any combination of the following: 1) composition of the substrate and plating (even when the plating and substrate having common elements); 2) analysis of thickness of the plating(s); 3) analysis of the depth of the plating(s), e.g., the thickness of any overlay; 4) analysis of the crystalline phase depth simultaneous with phase composition; 5) the preferred crystalline orientation; 6) the strain in the substrate; and (7) crystallinity and grain size. The apparatus is similar to that of U.S. Pat. No. 5,148,458 issued to Ruud, with the apparatus of this invention having the several detectors placed on different arcs and/or radial distances from the specimen surface under investigation.

21 Claims, 3 Drawing Sheets

OTHER PUBLICATIONS

*Nondestructive Characterization of Materials*, 1989, pp. 406–412.

C. O. Ruud, "X-Ray Analysis of Advances in Portable Field Instrumentation," *Journal of Metals*, vol. 31, No. 6, Jun. 1979, pp. 10–15.

SAE, "Residual Stress Measurement by X-Ray Diffraction," SAE J 784a, *Society of Automotive Engineers*, Warrendale, Pa., p. 14, FIG. 15, 1980.

C. F. Jatczak, "Retained Austenite and Its Measurement by X-Ray Diffraction," *Society of Automotive Engineers*, 1980.

Kopineck et al., "Texture Analyzer for On-Line $r_m$-Value Estimation," *Textures and Microstructures*, 1987, vol. 7, pp. 97–113.

Fricke et al., "A Practical Texture Measurement Instrument," ICOTOMB, edited by Kalland et al., *The Metallurgical Society*, pp. 257–262, 1988.

Ruud et al., "X-Ray Diffraction Measurement of Residual Stresses in Thick, Multi-Pass Steel Weldments," *Journal of Pressure Vessels Technology*, vol. 107, 1985.

METHOD AND APPARATUS FOR IN-PROCESS ANALYSIS OF POLYCRYSTALLINE FILMS AND COATINGS BY X-RAY DIFFRACTION

This application is a continuation-in-part of copending application application Ser. No. 08/020,480, filed Feb. 22, 1993 by Clayton O. Ruud et al and entitled "Method For In-Process Analysis Of Polycrystalline Films and Coatings By X-Ray Diffraction."

FIELD OF THE INVENTION

The present invention relates to characterization of platings, films, and coatings and, more particularly, to the use of position sensitive detectors to provide a real-time X-ray diffraction analysis of platings and coatings such as, for example, Pd:Ni alloy electroplate, zinc galvanneal coatings on steel, and vapor deposited materials. The apparatus and techniques may also find application in materials where platings are not extant.

BACKGROUND OF THE INVENTION

There is a great commercial need for stringent quality control of crystalline platings, films, coatings, and coating processes. Stresses and/or discontinuities in metal or ceramic coatings may lead to cracking, corrosion, peeling, or a myriad of other problems. More importantly, significant manufacturing cost reductions and improvements in quality and reliability can be achieved by insuring that 1) the applied coating thickness is not excessive for a specific application, and 2) the elemental and phase composition as well as the crystallite size and orientation are correct. Tighter control over the coating thickness and composition conserves raw material, and the cost savings can be great when the coating contains gold, silver, or other rare material.

Unfortunately, the above-described quality control of platings, films, and coatings which are electroplated, hot dipped, chemical vapor deposited, etc., is very difficult. (Note: for purposes of this application the terms "plating," "film," and "coating" will be used interchangeably).

The existing technique of X-ray fluorescence (XRF) e.g. U.S. Pat. No. 5,137,727 by F. Vogler does provide a limited capability for analyzing elemental composition and thickness, but this method is sometimes slow and unsuited for many coatings. Specifically, when other underlying platings or the substrate itself contain one of the electroplated alloy elements, XRF analysis yields ambiguous results. This is often the case with coatings such as Pd:Ni alloy. Hence, XRF analysis may be inadequate. Moreover, XRF does not provide information on phase composition, strains, or crystallite size, and orientation.

Whenever X-rays encounter a crystalline material, the regularly spaced atoms of the crystal diffract some of the X-rays. The characteristic diffraction pattern is indicative of the crystal structure of the material, and various properties of the material can be analyzed based upon particular features of the pattern. X-ray diffraction (XRD) analysis evolved from this basic premise, and XRD has proven to be a practical, non-destructive way of gaining a more complete analysis than is possible with, for example, XRF.

The basis for all XRD techniques is the Bragg relation, which equates the interplanar atomic spacing (d) of a material to the Bragg angle ($\theta$). The relation is as follows:

$$n\lambda = 2d\sin\theta$$

where,
n is usually unity for polycrystalline XRD,
$\lambda$ is the wavelength of diffracting X-rays,
d is the interplanar spacing of a particular Miller index, and
$\theta$ is the Bragg angle.

By comparing a measured diffraction pattern to standard patterns cataloged in a database, the material can be identified. Hence, XRD analysis holds great potential for on-line monitoring and quality control, and XRD has been used extensively to determine second phase composition in steels, alloy content in platings, and preferred orientation (texture) in copper alloy strip and aluminum sheet. XRD has also been used to measure residual stresses and texture in various metals including nickel platings. Also, XRD has been applied to texture assessment in steel sheet (in Germany) and to aluminum sheet stock (in the U.S.A.), in both instances using an energy dispersive X-ray detector. With a diffractometer, X-rays of predetermined wavelength are emitted from a source and are diffracted from a sample as shown in FIG. 1. The intensity of the diffracted X-rays is sensed by a detector which is moved continuously or step-wise along the diffraction angle. The sample or source is rotated (or "scanned") over one-half the diffraction angle (i.e., twice the Bragg angle $\theta$) to determine a diffraction pattern such as the exemplary NaCl pattern shown in FIG. 2. More recently, position sensitive detectors have been substituted for conventional detectors in some applications to eliminate the scanning. In either case, the resulting diffraction pattern may be used to identify the phase composition of the sample.

Originally, diffraction methods including XRD were possible only in the laboratory. As with XRF, the necessary XRD equipment was large, unwieldy, and required a great deal of time to operate. A complete scan took upward of ten minutes. This was unsuitable for on-line monitoring and quality control because it could not be used for real-time measurements.

A solution to the above-described problem became possible through the development of "position sensitive detectors" (PSDs). These detectors allow simultaneous measurement of diffracted X-rays over a range of $\theta$. Using a PSD, a two-dimensional intensity-position snap-shot can be obtained quickly, and no mechanical scanning operation is necessary.

Further progress toward on-line compositional analysis was made with the development of a Position Sensitive Scintillation Detector (PSSD). This device combines fiber optic and electrooptical technology into a unique position sensitive detector. See, Ruud, "X-Ray Analysis and Advances in Portable Field Instrumentation," *Journal of Metals,* pp. 10–15 (June 1979), Ruud, "A Unique Position Sensitive Detector For X-Ray Powder Diffraction," *Industrial Research and Development,* pp. 84–87 (June 1983), and U.S. Pat. Nos. 4,686,631 and 5,148,458 issued to Ruud (the above-referenced documents are herein incorporated by reference). The PSSD has been successfully employed for residual stress measurement of materials ranging from thick plate weldments to ceramic coatings and to copper alloy strip moving at near 400 fpm. In addition, the PSSD has been used for texture studies in metals, simultaneous stress, and phase analysis of bearing steels (see U.S. Pat. No. 5,148,458 issued to Ruud), and for alloy composition measurements in platings. This invention differs from that in U.S. Pat. No. 5,148,458 in that the radial position of the detectors is varied depending upon the position of the x-ray source focus, the angle of the incident x-ray beam to the plating and substrate surface, the diffraction angles and the orientations of the diffracting crystallographic planes to the specimen surfaces. Due to the fiber optics, the PSSD is very versatile and can be made compact and portable. This coupled with the real-time analysis capability of the PSSD renders it well-suited for on-line commercial applications.

Taken together, the PSSD and other prior art devices have been used to analyze compositions based on the peak positions and intensities appearing in the diffraction patterns for given samples. They have been used for residual stress measurement, but not all are well suited for this specialized purpose. Also, they have been used for basic single phase analysis of the composition of a stoichiometric compound as described previously.

However, platings and coatings often comprise multiple layers and, therefore, multiple phases. Preferred crystallite orientation of the multiple phases complicate the process of analysis based only on the peak positions and intensities as from a conventional diffraction pattern. Moreover, the substrate often diffuses into the coating, and this further complicates any attempted XRD analysis based solely on peak intensities from planes of a single orientation to the sample surface. For example, with galvanneal plated cold rolled steel sheet, the substrate diffuses into the zinc during the plating process and forms intermetallic and solid solution phases which may adversely affect subsequent processing. These phases can result in inconsistent and/or adverse behavior (i.e., cracking, flaking, and powdering) during the forming operation. Unfortunately, the use of XRD with conventional scanning and/or PSDs is usually too slow and the instrumentation too delicate to be used during plating processes. Hence, there is currently no reliable way to assure the quality of galvanized steel and other platings, and quality control of such platings is therefore hampered.

There would be great commercial advantage if the PSSD could be adapted to yield a real-time detailed analysis of samples having polycrystalline platings and, specifically, for real-time analysis of the following characteristics:

phase composition (including degree of alloying);
plating thickness;
phase composition of platings having elements in common with adjacent platings and/or the substrate;
crystalline phase depth;
crystallinity and grain size;
crystalline strain;
preferred crystalline orientation; and
simultaneous measurement of two or more of the above characteristics.

SUMMARY OF THE INVENTION

It is, therefore, an object of the present invention to provide an accurate, real-time, in-process device for the analysis of the character of platings, films, and coatings by X-ray diffraction.

It is another object of the invention to provide a complete characterization of platings, films, and coatings in accordance with the above-described object which is based not only on the peak positions appearing in a diffraction pattern at a single psi ($\psi$) angle, but also on the breadth and positions of the diffracted peaks and the relative intensities of different peaks at various psi ($\psi$) angles.

It is another object of the present invention to employ a Position Sensitive Scintillation Detector (PSSD) which incorporates fiber optic and electrooptical technology to analyze films, coatings, and platings in the above-described manner, and to thereby provide individual or simultaneous measurements of solid solution composition, crystalline phase composition, macro and micro strains, crystallinity, and crystallite size, and preferred orientation (crystallographic texture) of coatings.

It is a specific object of the present invention to provide a method for determining phase identification, phase composition (including degree of alloying), phase depth, thickness of platings, coatings and films, phase composition of platings, coatings and films having elements in common with adjacent coatings and/or the substrate, macro and micro strains, crystallinity and crystallite size, preferred crystalline orientation, simultaneous measurement of crystalline phase depth and phase composition, simultaneous measurement of macro and micro strains with any of the aforementioned characteristics, and simultaneous measurements of any two or more of the aforementioned characteristics.

The present invention comprises the method by which a PSD is adapted to provide a real-time analysis of a plated, coated, and/or a film specimen. The PSD of the present invention possesses two or more detector surfaces which may be positioned independently of one another for detecting X-rays diffracted from crystalline material at one or several ranges of Bragg angles and/or one or several ranges of psi ($\psi$) angles. The detection of Bragg angles, both in forward and back scatter diffraction are included. The method of using the PSD includes applying X-radiation to the specimen (which comprises at least one polycrystalline coating on a substrate), and measuring a spectra of diffracted peaks of X-radiation from the coating of interest and/or which have penetrated the coating of interest and diffracted from the substrate and/or underlying coatings to the PSD. The diffracted data is analyzed and compensated for confounding diffraction phenomena occurring in both the coating and substrate. Finally, the spectra are processed to yield the desired information from the plating (even when the coating and substrate have common element and/or confounding information such as texture and varying phase composition exists).

The processing may be expanded to yield any one or a combination of characteristics mentioned previously in these teachings.

BRIEF DESCRIPTION OF THE DRAWINGS

Other objects, features, and advantages of the present invention will become more apparent from the following detailed description of preferred embodiments and certain modifications thereof when taken together with the accompanying drawings in which.

DETAILED DESCRIPTION OF THE PREFERRED EMBODIMENT(S)

Diffraction patterns are measured according to the invention using a Position Sensitive Detector (PSD), which is a relatively new and often preferred type of X-ray detector. A Position Sensitive Scintillation Detector (PSSD) is one example of such a device, see, Ruud, "A Unique Position Sensitive Detector For X-Ray Powder Diffraction," *Industrial Research and Development*, pp. 84–87 (June 1983), U.S. Pat. Nos. 4,686,631 and 5,148,458. The above-described article and patent are herein incorporated by reference. A commercial PSSD is available from Denver X-ray Instruments, Inc., of Altoona, Pa.

Figure 1:
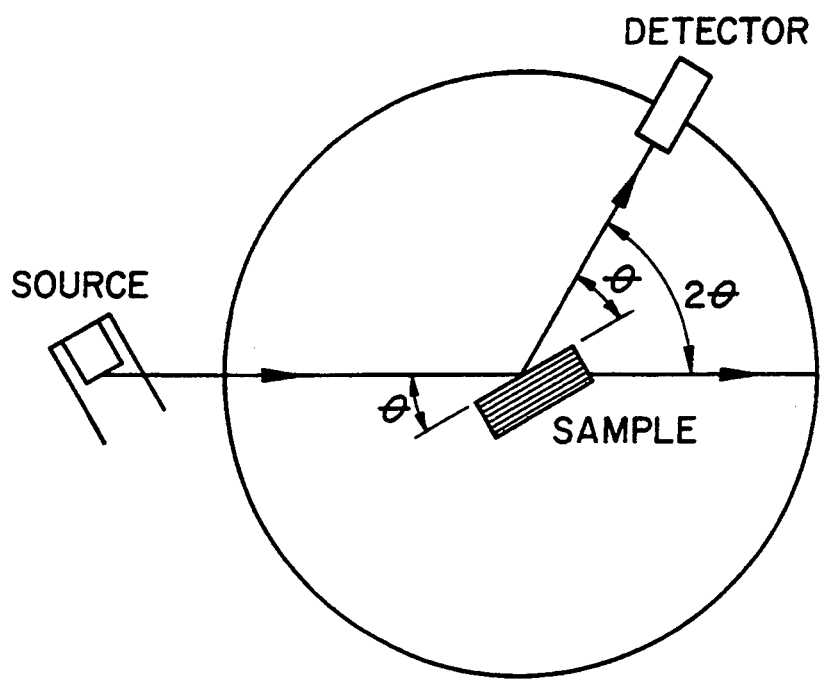
FIG. 1 is a perspective view showing the operation of a conventional diffractometer wherein X-rays are emitted from the source, are diffracted from the sample, and the diffracted X-rays are sensed by a scanning detector.
Figure 2:
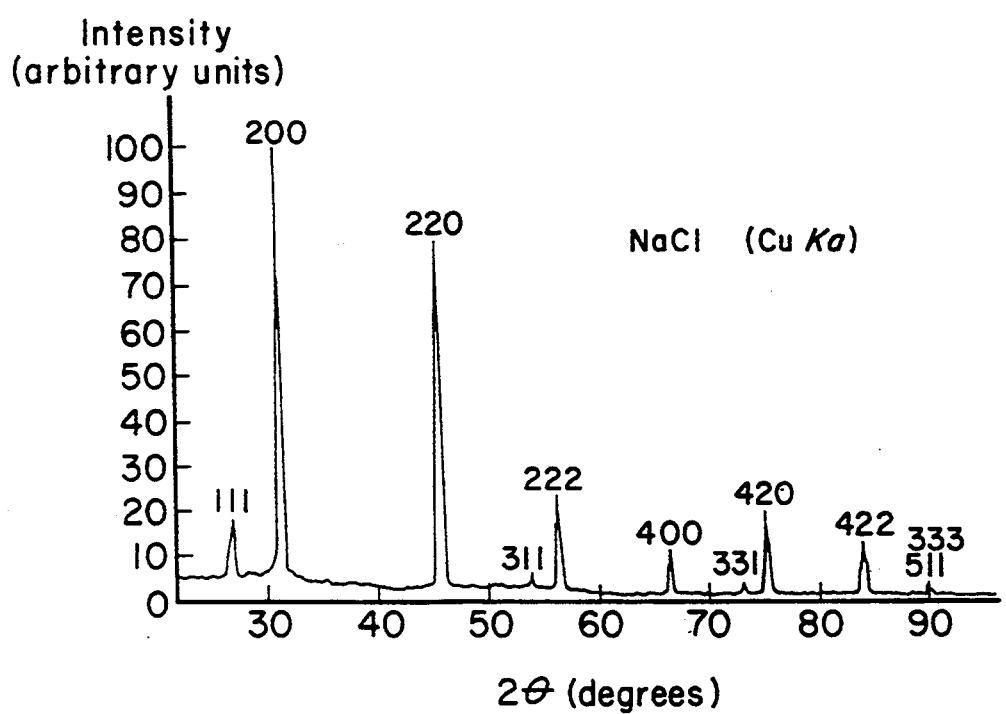
FIG. 2 is an exemplary diffraction pattern for NaCl obtained by use of a diffractometer as in FIG. 1.
Figure 3:
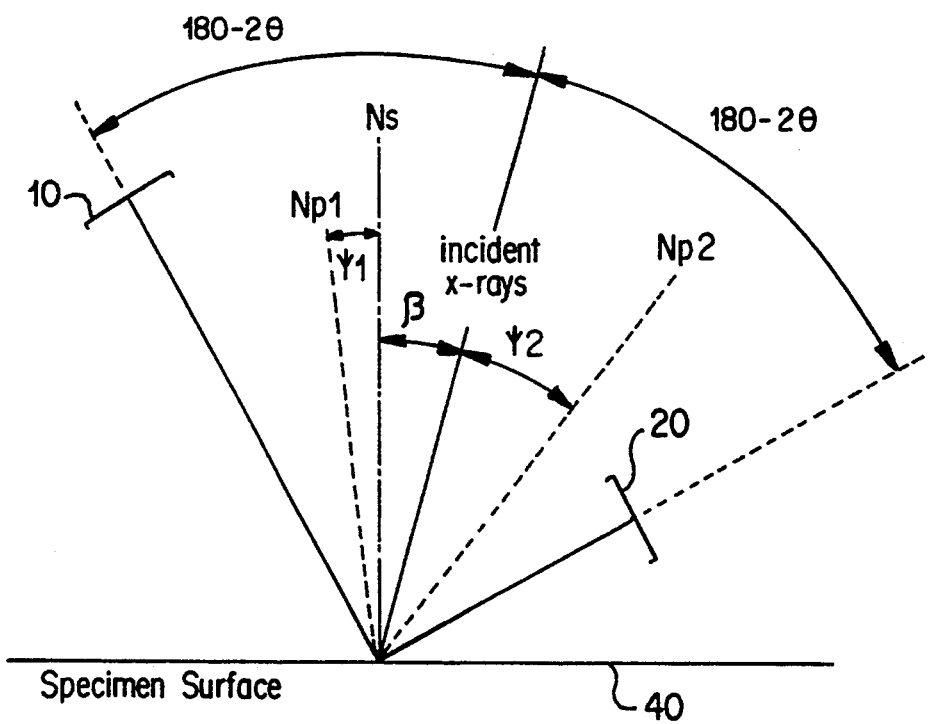
FIG. 3 shows a PSSD arranged for analysis of Pd:Ni alloy electroplate coatings according to one embodiment of the present invention.

FIG. 3 illustrates one exemplary PSSD arrangement in accordance with the present invention wherein scintillation coated coherent fiber optic detectors 10, 20 are positioned on both sides of an incident X-ray beam 30. It should be noted that fiber optic detectors 10 and 20 may be independently positioned, and each may be on the same or opposite sides of the incident X-ray beam 30. The fiber optic detectors 10 and 20 are coupled via an optical amplifier to silicon diode arrays. The diode arrays convert the amplified coherent optical signals into electrical signals which are then transmitted to a central processor or computer. It should be noted that other types of position-sensitive detectors 10, 20 may be used to achieve the same results, for example, charge-coupled devices (CCDs) or other one-dimensional or two-dimensional X-ray sensitive devices may be used.

The exemplary detector 10, 20 arrangement shown in FIG. 3 is a back-reflection camera geometry which is a modification of the conventional Seemann-Bohlin camera geometry. The SET technique takes advantage of the fact that X-rays are diffracted in a cone centered around the incident beam. The detectors 10, 20 of FIG. 3 are positioned to intercept the diffracted X-rays in selected segments of this cone. The conventional geometry is modified by placing the incident X-ray beam at an angle to the specimen surface 40 such that crystallographic planes at two or more psi angles $\psi_1$, $\psi_2$ relative to the specimen surface 40 may be detected simultaneously. In platings, the crystallites often have a preferred orientation, thus the X-ray intensity may change with the angles $\psi_1$, $\psi_2$. Therefore, using two or more position-sensitive detectors each at different $\psi$ angles has an advantage in that the degree of preferred orientation present can be monitored as well as phase composition.

There are many advantages to the PSSD technology which enhance its suitability for on-line consideration. One advantage is the speed of data collection. An X-ray pattern from steel over about forty degrees of angle may take less than one to a few seconds to collect using the PSSD. The same pattern would take ten to twenty minutes to collect with a conventional scanning instrument. The high measurement speed of the PSSD is well-suited for on-line applications. In addition, the PSSD detector can be adapted to various configurations since it is solid state and compact. Flexible fiber optic ribbons connect the X-ray detectors 10, 20 (FIG. 3) to a central processor or computer through electro-optical devices, and the fiber optic ribbons can be made several feet long. This allows for a wide variety of combinations of angles, distances, and orientations of ribbon detectors in a single analytical arrangement to monitor several characteristics of the plating(s). Also the electronic components may be located some distance from the process being monitored. This also provides for ease of relocation of the X-ray detection surface while the electronics remain stationary. For example, a plurality of PSSD detectors may be used to measure elemental composition or other characteristics in one or more crystallographic phases.

The invention encompasses the method by which the above-described PSSD can be employed to provide a comprehensive real-time analysis of a specimen comprising one or more crystalline platings, films, or coatings on a substrate.

Figure 4:
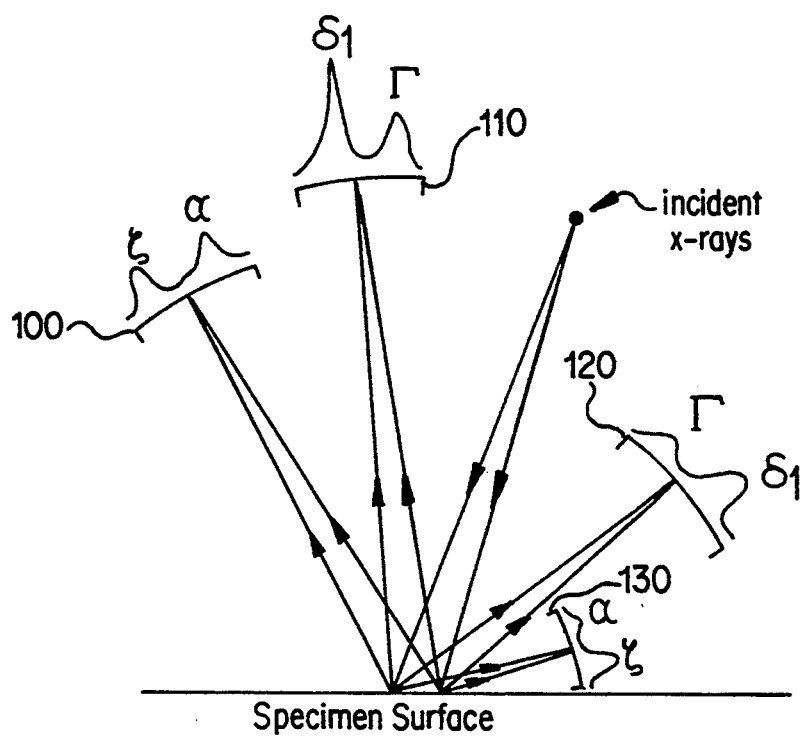
FIG. 4 shows a PSSD arranged with four fiber optic detectors 100, 110, 120, and 130 for on-line characterization of galvanneal coating according to a second embodiment of the present invention.
Figure 5:
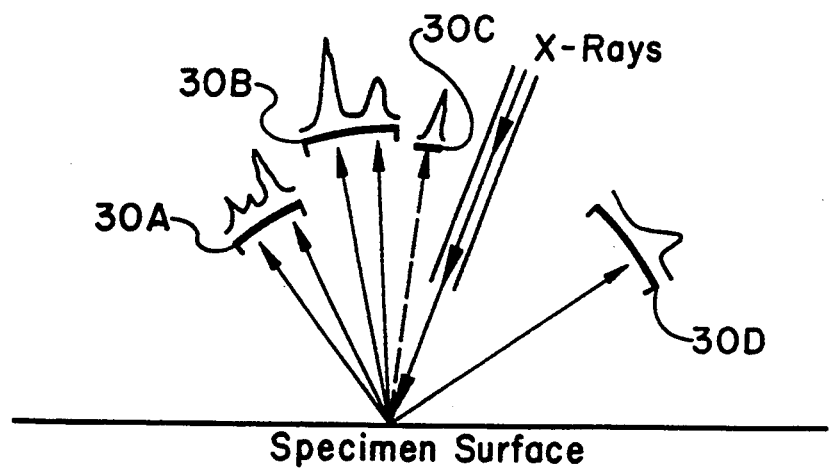
FIG. 5 shows a PSSD arranged with four fiber optic detectors, 30A, 30B, 30C, and 30D in a third alternative arrangement where detector 30D is not on the same plane as detectors 30A, 30B, and 30C; such types of arrangements provide for more versatility in situations where texture exists.

In general, the analysis begins by measuring one or more selected (h, k, l) X-ray diffractions from plating (or platings) and sometimes the substrate. In addition to the exemplary arrangement shown in FIG. 3, two other possible detector arrangements are shown in FIGS. 4 and 5 which both incorporate four fiber optic detectors. The arrangement of FIG. 4 shows a PSSD arrangement with four fiber optic detectors 100, 110, 120, and 130 for on-line characterization of galvanneal coating. The arrangement of FIG. 5 includes four fiber optic detectors, 30A, 30B, 30C, and 30D, and detector 30C is not on the same plane as detectors 30A, 30B, and 30D. The arrangement of FIG. 5 is especially suited for instances where texture exists.

In all cases, the diffracted peaks from the crystalline (poly or single) substrate may be used to determine strain in that material induced by the plating (film or coating) or platings and/or as reference information for analysis of characteristics of the film. For example, the intensity of the substrate peaks may be used to determine the thickness and/or composition of the plating(s); where thickness and composition are both to be measured, they could be distinguished through use of more than one psi ($\psi$) angle and application of two or more simultaneous equations in the analysis. Comparison of position of the peaks from the substrate from two or more psi ($\psi$) angles could be used to determine strain in the diffracting material and the average could be used as a reference Bragg angle for analysis of composition and phase identification of the plating(s).

The diffracted peaks from the plating or platings could be used to determine the strain in that material through comparison of two or more psi ($\psi$) angles, and/or by comparison with substrate diffracted peak position(s). The average psi ($\psi$) angle (hkl) Bragg angle for a given phase from the plating may be compared with the average Bragg angle from the substrate to identify crystalline phases in the plating or determine the composition of a solid solution phase. The intensity of the plating's diffracted peaks may be compared with peaks from the substrate to determine the thickness and/or quantitative composition of the plating, the latter when more than one phase was present in the plating. If peaks from more than one psi ($\psi$) angle are available, some type of averaging of these may be used for thickness and composition, or combinations of these to provide simultaneous equations.

Where crystalline texture is present, the detector arrangement of FIG. 5 may be employed. The arrangement of FIG. 5 includes four fiber optic detectors, 30A, 30B, 30C, and 30C, and detector 30D is not on the same plane as detectors 30A, 30B, and 30D.

FIG. 4 shows position sensitive detectors at various radii from a common center. This configuration is important in that it provides for location of detectors near the optimum focal distance and angle for the different arcs characterized by the focusing conditions of the various crystallographic (h,k,l) planes at different orientations (psi angles) to the surface that are necessary for analysis of the samples. The variation of focusing conditions with psi ($\psi$) angle is known in x-ray stress analysis, see for example pages 457 and 458 of *Elements of X-Ray Diffraction*, 2nd Edition, by B. D. Cullity but has not been applied to applications for position sensitive detectors. It is necessary to use different radii to optimize the clarity and definition of the diffracted spectra.

Figure 6:
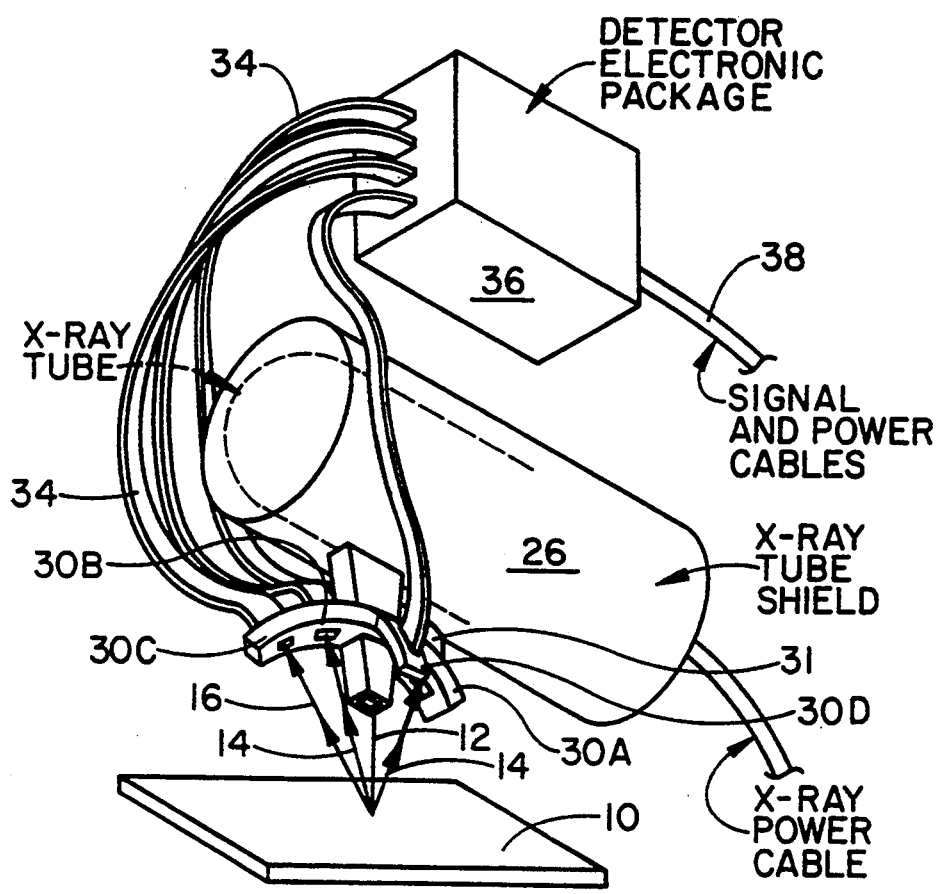
FIG. 6 illustrates another arrangement with four fiber optic detectors 30A, 30B, 30C, and 30D, which is similar to FIG. 5 but is a perspective view showing an additional support arm 31 for carrying the detector 30C used in the arrangement of FIG. 5.

FIGS. 3 and 5 also show that optimization of clarity and definition of the diffracted spectra is realized by placing the detectors at different distances (radii) from the specimen. In practice, the detectors 30A, 30B, and 30D of FIG. 6 are not on the same circular arc or radial distance but are shown so as to emphasize the location of detector 30C as lying in a plane other than the plane containing detectors 30A, 30B, and 30D. The detectors receive X-rays diffracted from different h,k,l planes from one or more crystalline species in the specimens.

If the radial and arc position of the detectors are not optimized the diffracted x-ray peaks would be so diffuse that they would tend to overlap with each other; thereby rendering the detected signal useless. For example, without suitable adjustment of the radial position of the detector, the three peaks illustrated as detected by 30A in FIG. 5 might be detected as two asymmetric broad peaks. Or from detector 30B the two peaks might be detected as a single asymmetric broad peak. These situations would so confuse the data that analysis would be of little use.

The arrangement of FIG. 5 can be accomplished by modifying a conventional PSSD such as shown and described in U.S. Pat. No. 5,148,458.

FIG. 6 illustrates the modified PSSD as described above. The modification may be accomplished with additional support arm(s) such as arm 31 on which the non-planar detector 30C is mounted.

The above-described arrangement is especially suited for instances where texture exists. The intensity of various (hkl) peaks from the plating, or platings, would be compared, and/or the intensity from a given (hkl) peak at two or more psi ($\psi$) angles or phi angles ($\Phi$). See, e.g., SAE, *Residual Stress Measurement By X-Ray Diffraction*, SAE J 784a, Society of Automotive Engineers, Warrendale, Pa., p. 14, FIG. 15 (1980). The intensity of diffracted (hkl) peaks from a given phase at various psi ($\psi$) and/or phi ($\Phi$) angles also may be used to establish the phase depth in the plating, provided a sufficient number of psi ($\psi$) and/or phi ($\Phi$) attitudes of (hkl) diffractions were available.

Finally, polycrystalline microstrain and grain size can be determined through analysis of the breadth of the peaks; by comparing the breadth of two or more (hkl) diffractions or the shape of a single diffraction. Crystallinity can be determined by comparing the intensity of amorphous scattering over a selected Bragg angle range with X-ray peaks diffracted from crystalline phases.

In sum, by employing a PSD in conjunction with the above-described arrangement and analysis, the entire comprehensive evaluation of the plating and substrate may be evaluated in real-time, and the following data can be ascertained:

1. Composition of the substrate and plating (even when the plating and substrate have common elements).
2. Analysis of thickness of plating or platings.
3. Analysis of depth of phases in platings or plating.
4. Analysis of crystalline phase depth simultaneous with phase composition.
5. Preferred crystalline orientation.
6. Strain in the substrate and platings.
7. Crystallinity and grain size.
8. Any combination or combinations of the above (simultaneously).

As a detailed example of the above-described use of the PSSD according to the present invention, two exemplary analyses will now be presented. These include an analysis of galvannealed platings on sheet steel and an analysis of Pd:Ni alloy electroplate on a copper alloy substrate.

ANALYSIS OF PD:NI ALLOY ELECTROPLATE

In the preferred embodiment, a PSSD instrument is used and is arranged for the simultaneous collection of the Cu alloy substrate peak and the Pd:Ni alloy peak. The X-radiation used is CrK$\alpha$, which has a wavelength of approximately 2.29 angstroms. All of the data necessary for analysis can be collected in under fifteen seconds, depending on the X-ray tube power supply, detector components, and X-ray focusing geometry. No mechanical movement of the detector, X-ray source, or sample is necessary for complete data collection, although the sample could be moving as in a manufacturing process. The diffracted peaks from both the alloy plating and the substrate are measured with respect to the (220) Miller index planes of the substrate.

The Pd:Ni alloy composition is determined in a multistep process.

First, the Cu alloy substrate is characterized for X-ray peak position with CrK$\alpha$ radiation which penetrates the thin Pd:Ni alloy plating and diffracts from the Cu alloy substrate to the PSSD. At the same time, the Pd:Ni alloy is characterized for X-ray peak position of the diffracted CrK$\alpha$ radiation. The Cu substrate diffraction determines the residual stress in the Cu alloy, and this is determined by the single exposure technique (SET) illustrated in FIG. 3. Generally, the Cu substrate will diffract at 127.4 degrees and the Pd:Ni alloy plating will diffract in a range of between 112 and 120 degrees, depending upon the alloy content. The radial position of the position sensitive detectors, 10 and 20 in FIG. 3, is determined by the diffraction angles, the position of the x-ray source focus, the angle of the incident x-ray beam to the plating surface, and the orientation of the diffracting crystallographic planes to the plating surface; see *Elements of X-Ray Diffraction* 2nd Ed., by B. D. Cullity.

Second, the diffraction angles are reduced to yield the Bragg angle of diffraction $\theta$ and the interatomic spacings d.

Third, the data is corrected for residual stresses in the substrate and platings, and from the corrected values the Pd content of the electroplate plating is calculated using a known relation between composition and interatomic spacing d. The following corrections and calculations may be evaluated in real-time by any suitable computer.

The difference between the Bragg angle measured from the Cu alloy substrate $\theta_s$ less the Bragg angle for the unstressed Cu alloy $\theta_{so}$ is calculated as:

$$\Delta\theta = \theta_s - \theta_{so}.$$

The difference $\Delta\theta$ is a correction factor for residual stress effects. This correction varies with $\psi$, the angle between the diffracting plane normal and the specimen normal. Thus, the correction factor must be calculated for each $\psi$ angle.

Since the PSSD outputs peak position in pixel units, it is convenient to convert $\Delta\theta$ by the following chord length calculation into a pixel unit:

$$\Delta \text{ pixel} = R_o \sin(2\Delta\theta)$$

where, $R_o$ is the specimen to detector distance.

Once $\Delta\theta$ is known as a pixel unit ($\Delta$pixel), the result can be used to correct the Cu alloy peak position for residual stress using the following equation:

$$\text{Pixel Ref.} = \text{Cu Alloy} + \Delta\text{pixel},$$

where Cu Alloy is the measured Cu alloy peak position.

This yields the pixel peak position for $\theta_{so}$ of the Cu alloy, termed "pixel reference."

Finally, the Pd:Ni composition is calculated. The equations for the calculations follow:

$$\Delta\text{Cu} - \text{Pd:Ni} = \text{Pixel Ref.} - \text{Pd:Ni Position}$$

where,

Pd:Ni Position is the position of the Pd:Ni peak on the detector, and $\Delta$Cu-Pd:Ni is the pixel difference from the Cu alloy reference peak to the Pd:Ni peak. where, $$\Delta 2\theta = \sin^{-1}\left[\frac{\Delta\text{Cu} - \text{Pd:Ni}}{R_o}\right]$$

$\Delta 2\theta$ is the difference between the Cu alloy and the Pd:Ni diffraction angles.

$\theta_{pd:Ni}$ is then found as follows by subtracting $\frac{1}{2} \Delta 2\theta$ from $\theta_{so}$ for the Cu alloy:

$$\Theta_{Pd:Ni} = \Theta_{oCuAlloy} - \frac{\Delta 2\Theta}{2}$$

where, $\theta_{Pd:Ni}$ is the Bragg angle for the Pd:Ni plating, $\theta_{oCuAlloy}$ is the unstressed Bragg angle for the Cu alloy, The stress in the Pd:Ni plating can be determined by the following equation using the single exposure method, since two $\psi$ angles and corresponding $\theta$'s are known:

$$\sigma_{SET} = \left(\frac{E}{1+\nu}\right)\left(\frac{\theta_L - \theta_R}{2\sin^2\theta_o \sin 2\beta}\right)$$

where, $\sigma_{SET}$ is the stress calculated by the single exposure technique, E is the elastic modulus for the specific crystallographic direction, $\nu$ is Poisson's ratio, $\theta_L$ and $\theta_R$ are the Bragg angles measured on the left and right detectors, $\beta$ is the angle of the incident X-rays with respect to the surface normal.

Once stress has been calculated, the change in interatomic spacing due to stress can be determined by solving the following equation:

$$\Delta d = d_{\psi L}\sigma_{SET}\left(\frac{1+\nu}{E}\right)\sin^2\psi$$

where, $d_o$ is assumed to be approximately $d_{\psi L}$. This is a reasonable assumption since $\Delta d \ll d$, $d_{\psi L}$ is the interatomic spacing measured at the $\psi$ angle of the left detector 20 of FIG. 3, $\psi$ is the angle between the diffracting planes normal and the surface normal.

Then, the following equation is solved to find the interatomic spacing $\Delta d$ after stress correction:

$$d = d_{\psi L} + \Delta d$$

The lattice parameter a can be calculated from d using the following equation:

$$a = \sqrt{d^2 \times (h^2 + k^2 + l^2)}$$

where, a is the lattice parameter of the plating, d is the interatomic spacing of a specific miller index (hkl), h, k, and l are the components of the miller index.

Finally, a can be used to calculate %Pd using the following relationship between compositions of a Pd:Ni alloy and the lattice parameter:

$$\%\text{Pd} = -Aa^2 + Ba + C$$

where,

A, B, and C are constants determined from crystallographic reference data of the effect of composition (Pd:Ni ratio) on the lattice parameter a. For selected data, A, B, and C were found to be $-159.94$, $-1460.4$, and $-1360.7$, respectively.

%Pd is the weight percent PD in the alloy plating.

Using the PSSD and above-described procedures according to the method of the present invention, the Pd content of Pd electroplate may successfully be evaluated in real-time with excellent precision.

ANALYSIS OF GALVANNEALED PLATINGS ON SHEET STEEL

The above-described PSSD may also be used in accordance with the present invention for on-line measurement of the phase composition of galvannealed platings on sheet steel, as well as to measure the average iron content of the plating.

A number of factors must be considered in adapting the PSSD to the on-line characterization of galvanneal plating. A vital concern is the proper selection of X-radiation wavelength. In the preferred embodiment, a copper target X-ray tube is used to produce an intense peak of CuKα radiation. However, other tube targets may be used, including Co, Ni, or Mo. CuKα will penetrate about 16 μm of zinc before it is fifty percent absorbed, and this results in sufficiently intense diffraction for the galvannealed application. With CuKα radiation, deployment of four fiber optic detectors 100, 110, 120, and 130 at Bragg angles of 74, 71, 67, and 68 degrees, respectively, the Γ, $\delta_1$, ξ, and α-Fe phases would be detected as shown. The preferred detector arrangement is shown in FIG. 4 where the radial and arc position of each detector 100, 110, 120, and 130 is determined by the diffraction angles, the position of the x-ray source focus, the angle of the incident x-ray beam to the plating surface, and the orientation of the diffracting crystallographic (h,k,l) planes to the plating surface; see *Elements of X-Ray Diffraction* 2nd Ed., by B. D. Cullity. The detectors may also be contoured depending upon the focusing circle curvature.

Using the PSSD, the plating composition is determined in a multi-step process.

First, the sheet steel substrate is characterized for X-ray peak position with CuKα radiation which penetrates the thin galvanneal plating and diffracts from the substrate to the PSSD. At the same time, the galvanneal plating itself is characterized for X-ray peak position with the CuKα radiation.

Second, the diffraction angles are determined from the X-ray peak positions to yield the Bragg angle of diffraction θ.

Third, the data may be corrected for residual stresses in the substrates and platings as described previously, and the corrected values are processed to identify the phase composition of galvannealed plating, as well as the average iron content of the solid solution phase of the plating.

The phases present in galvanneal platings each have a specific crystal structure with different crystal lattice constants. Consequently, each phase diffracts X-ray peaks at specific Bragg angles. By comparing the obtained diffraction pattern to a database of standard patterns, phases contained in the plating can be identified. Also, the variation of elemental content within a phase can be determined from the X-ray peak breadth.

The volume fraction of each phase can be determined by relative X-ray peak intensity. The greater the volume of a particular phase that is present, the higher its diffracted peak intensity. However, the position, i.e., depth of the phase within the plating, would also influence the intensity. The depth of the particular phase in the plating can be estimated by comparing the intensities of the peaks on the fiber optic detectors at high and low ψ angles. The high ψ would show a lower intensity. This is because the intensity depends on the phase's depth in the plating. The relative intensity of peaks from a given phase on two detectors would change consistently as the relative depth of the phase in the plating changed. Also, the variation of elemental content within a phase can be determined from the X-ray peak breadth.

Having now fully set forth the preferred embodiments and certain modifications of the concept underlying the present invention, various other embodiments as well as certain variations and modifications of the embodiments herein described will obviously occur to those skilled in the art upon becoming familiar with said underlying concept. It is to be understood, therefore, that within the scope of the appended claims, the invention may be practiced otherwise than as specifically set forth herein.

We claim:

1. A method for real time analysis of a plated specimen the method including the steps of arranging two or more position sensitive detector surfaces with at least one first said detector surface positioned on either side of an incident x-ray beam and at least one second said detector surface positioned on either side of said incident x-ray beam for detecting x-rays diffracted from a plurality of crystallographic planes of said specimen at various angles, said detector surfaces positioned at different distances from said specimen, said method comprising the steps of:

applying x-radiation to a specimen comprising at least one polycrystalline plating on a substrate;

measuring the spectra of diffracted peaks of said x-radiation diffracted from said at least one plating or substrate to said detector surfaces; and processing said spectra to yield an elemental content of the phase or phases of said at least one plating.

2. The method according to claim 1 further comprising the step of compensating said measured spectra for residual stresses occurring in said at least one plating and substrate, and whereby said processing step further comprises processing said compensated spectra to yield an elemental content of the phase or phases of said plating.

3. The method according to claim 1 further comprising the step of processing said spectra to yield a thickness of said at least one plating.

4. The method according to claim 1 further comprising the step of processing said spectra to identify a crystalline phase composition within said at least one plating.

5. The method according to claim 4 further comprising the step of processing said spectra to determine a depth of said crystalline phase or phases within said at least one plating.

6. The method according to claim 4 further comprising the step of processing said spectra to determine a crystalline size of the phase or phases of said at least one plating.

7. The method according to claim 1 further comprising the step of processing said spectra to determine the crystalline orientation of the phase or phases of said at least one plating.

8. The method according to claim 1 further comprising the step of processing said spectra to determine a crystallinity of the phase or phases of said at least one plating.

9. The method according to claim 1 further comprising the step of processing said spectra to determine a microstrain in the phase or phases of said at least one plating.

10. An apparatus for real time analysis of a plated specimen, said apparatus including a plurality of position sensitive detector surfaces, an x-ray source for directing an incident beam of x-rays toward a plated specimen, said plural detector surfaces arranged with at least one first of said detector surfaces positioned on either side of an incident x-ray beam produced by said x-ray source and at least one second of said detector surfaces positioned on either side of said incident x-ray beam for detecting x-rays diffracted from a plurality of crystallographic planes of said plated specimen at various angles, said first and second detector surfaces positioned at different distances from said specimen, means for analyzing the spectra of diffracted peaks of x-radiation diffracted from said plurality of crystallographic planes of said plated specimen.

11. The method for real time analysis of a plated specimen, the method including the steps of arranging first and second position sensitive detector surfaces such that said first and second detector surfaces are positioned at different distances from said specimen, said specimen comprising at least one polycrystalline plating on a polycrystalline substrate wherein said at least one plating and said substrate contain a common element, and said detector surfaces being arranged with a first detector surface on either side of an incident X-ray beam and a second detector surface on either side of said incident X-ray beam for detecting X-rays diffracted from a plurality of crystallographic planes of said spectrum at respective angles, said method comprising the steps of:

applying X-radiation to said specimen;

measuring peaks of said x-radiation diffracted from said at least one plating or substrate back to said detector surfaces; and processing said spectra to yield an elemental content of the phase or phases of said plating or platings.

12. The method according to claim 11 further comprising the step of compensating said measured spectra for residual stresses occurring in said at least one plating and substrate, and whereby said processing step further comprises processing said compensated spectra to yield an elemental content of the phase or phases of said plating or platings.

13. The method according to claim 11 further comprising the step of processing said spectra to determine a thickness of said at least one plating.

14. The method according to claim 11 further comprising the step of processing said spectra to identify a crystalline phase composition within said at least one plating.

15. The method according to claim 11 further comprising the step of processing said spectra to determine a depth of said crystalline phase or phases within said at least one plating.

16. The method according to claim 11 further comprising the step of processing said spectra to determine a preferred crystalline orientation of crystalline phase.

17. The method according to claim 11 further comprising the step of processing said spectra to determine a crystallite grain size of the phase or phases of said at least one plating.

18. The method according to claim 11 further comprising the step of processing said spectra to determine a crystallinity of the phase or phases of said at least one plating.

19. The method according to claim 11 further comprising the step of processing said spectra to determine a microstrain in the phase or phases of said at least one platings.

20. A method for real time analysis of a plated specimen, the method including the steps of arranging two or more position sensitive detector surfaces with at least one first said detector surface positioned on either side of an incident x-ray beam and at least one second said detector surface positioned on either side of said incident x-ray beam for detecting x-rays diffracted from a plurality of crystallographic planes of said specimen at various angles, said detector surfaces positioned at different distances from said specimen, said method comprising the steps of:

applying x-radiation to a specimen comprising at least one polycrystalline plating on a substrate;

measuring the spectra of diffracted peaks of said x-radiation diffracted from said at least one plating or substrate to said detector surfaces;

processing said spectra to yield simultaneously at least two of: an elemental content of the phase or phases of said at least one plating, the thickness of said at least one plating, the crystalline phase composition within said at least one plating, the depth of said crystalline phase or phases of said plating, the crystalline size of the phase or phases of said at least one plating, the crystallinity of the phases or phases of said plating, the microstrain in the phase or phases of said at least one plating, and a preferred crystalline orientation of said phase or phases of said at least one said plating.

21. The method of claim 20 further comprising the step of compensating said measured spectra for residual stresses occurring in said plating and substrate, and whereby said processing step further comprises processing said compensated spectra.

* * * * *